United States Patent [19]

Strande

[11] 4,141,985

[45] Feb. 27, 1979

[54] ALLEVIATION OF MINIMAL BRAIN DYSFUNCTION WITH 2-[(3,4-DICHLOROPHENOXY)METHYL]-2-IMIDAZOLINE

[75] Inventor: Carl S. Strande, Midland, Mich.

[73] Assignee: The Dow Chemical Company, Midland, Mich.

[21] Appl. No.: 851,911

[22] Filed: Nov. 16, 1977

Related U.S. Application Data

[63] Continuation-in-part of Ser. No. 730,546, Oct. 7, 1976, abandoned.

[51] Int. Cl.$^2$ ............................................. A61K 31/415
[52] U.S. Cl. .................................................. 424/273 R
[58] Field of Search ........................................... 424/273

[56] References Cited

U.S. PATENT DOCUMENTS

| | | | |
|---|---|---|---|
| 3,449,355 | 6/1969 | White | 260/309.6 |
| 3,860,719 | 1/1975 | Marshall | 424/273 |

OTHER PUBLICATIONS

Sprague et al., Pediatric Clinics of N. America, vol. 20, No. 3, 719–735 (1973).
Krager et al., N.E.J. Med. 201(21); 1118–1120, Nov. 21, 1974.
Weiss et al., CMA Journal, vol. 104, pp. 20–25 (1971).
Physicians Desk Reference 29th Ed. (1975), pp. 709–710.
Chien & Kaplan, Curr. Therap. Res., 11(7), 471–474 (1969).
Chien & Kaplan, Curr. Therap. Res., 13(6), 350–352 (1971).
Fink & Irwin, Curr. Therap. Res., 18(4), 590–596 (1975).

*Primary Examiner*—Stanley J. Friedman

[57] ABSTRACT

A method useful for alleviating minimal brain dysfunction in humans comprises internally administering to a human an effective amount of 2-[(3,4-dichlorophenoxy)methyl]-2-imidazoline or a pharmaceutically-acceptable salt thereof.

3 Claims, No Drawings

ALLEVIATION OF MINIMAL BRAIN DYSFUNCTION WITH 2-[(3,4-DICHLOROPHENOXY)METHYL]-2-IMIDAZOLINE

CROSS REFERENCE TO RELATED APPLICATION

This is a continuation-in-part of my copending application Ser. No. 730,546, filed Oct. 7, 1976 and now abandoned.

BACKGROUND OF THE INVENTION

2-[(3,4-Dichlorophenoxy) methyl]-2-imidazoline and its pharmaceutically acceptable salts are known to have antidepressant and barbiturate antagonist activity (White, U.S. Pat. No. 3,449,355) and alcohol antagonist activity (Marshall U.S. Pat. No. 3,860,719). The compound is generically known as "fenmetozole." Fenmetozole and its salts have a favorable low toxicity. Fenmetozole hydrochloride has been administered to adult humans, both normal subjects and schizophrenic and/or depressed patients at dosages of 250 to 450 milligrams fenmetozole hydrochloride per day for 3-4 weeks. (Chien and Kaplan, Curr. Therap. Res. 11,471-474 (1969) and 13,350-352 (1971)) and has also been administered to normal adults at single dosages ranging from 25 to 250 milligrams with no ill effects reported other than a "tingling sensation" on the skin reported by some of the subjects, decreased heart rate and increased blood pressure at high dose level, Fink, Curr. Therap. Res. 18, 590-596 (October 1975).

Minimal Brain Dysfunction ("MBD") is a recognized neuropathological condition occurring in children, characterized by symptoms including hyperkinesis, chronic short attention span, distractibility, emotional lability and a characteristic electroencephalogram ("EEG"). Ethiology is unknown and diagnosis requires discrimination between MBD and similar behavioral symptons due to environmental factors (such as diet) and/or primary psychiatric disorder. EEG analysis is thus a significant factor in differential diagnosis. Over the last ten years, stimulant drugs have assumed a major role in the treatment of children with Minimal Brain Dysfunction. The synthetic sympathomimetic amines (especially methylphenidate) are known to be particularly useful. Recent advances in electrophysiology, utilizing specialized equipment and computerized measurement, permit the precise evaluation of various forms of brain dysfunction and abnormality. The practical application of these techniques permit: assessment of neuropathology, evaluation of drug effects, and assessment of sensory function and cognitive processes with a high degree of objectivity.

SUMMARY OF THE INVENTION

It has now been discovered that 2-[(3,4-dichlorophenoxy)methyl]-2-imidazoline (fenmetozole) and its pharmaceutically-acceptable salts are useful in alleviation of Minimal Brain Dysfunction in children. The invention thus concerns the internal administration to children suffering from Minimal Brain Dysfunction ("MBD") an amount of fenmetozole or a pharmaceutically-acceptable salt thereof sufficient to alleviate the Minimal Brain Dysfunction. In a preferred embodiment, the compound fenmetozole hydrochloride is administered orally to children between the ages of about 5 and 15 years and exhibiting symptoms of MBD, (diagnosed or diagnosable symptoms preferably including characteristic EEG changes) in an amount effective to reduce one or more of the MBD symptoms. Preferably, the amount is about 0.5 to 10 milligrams of fenmetozole hydrochloride per kilogram of body weight per day.

DETAILED DESCRIPTION

In the practice of the invention, fenmetozole or a specified salt is administered internally to a human child having MBD. The child under treatment is one of an age at which MBD is manifested, normally from about 5 or 6 to about 15 years of age. The child is also one suffering from MBD, that is, conditions such as hyperkinesis, learning disability, chronic short attention span. Diagnosis should include EEG analysis, and should be carefully conducted to differentiate between MBD and other conditions. Also, blood pressure determinations should be made and non-hypertensive children with MBD (normal blood pressure or hypotension) are preferred subjects to those having MBD with hypertension.

The compound can be administed orally or by injection or suppository, but oral administration is generally preferred. The exact dosage to be administered will vary somewhat from subject to subject depending on factors such as exact compound, dosage form and route of administration employed; age, size and weight of child; time and frequency of administration, etc. The dosage and regimen to be used in particular cases can be ascertained by conventional procedures, such as the use of EEG analysis to follow the effect of different dosages. In general, an effective dose will be from about 0.5 to about 10 milligrams of compound per kilogram of body weight per day, administered singly or, preferably in multiple divided dosages (e.g. two doses morning and noon. Preferably, the dosage administered either on a daily basis or at a given time (whether as the entire daily dose or a portion thereof) is also kept below an amount which produces serious, non-transitory increases in blood pressure. Preferred effective dosages are in the range of from about one to about five milligrams per kilogram per day with individual divided doses being between about 0.5 and about 3 mg/kg.

The following example is illustrative.

EXAMPLE 1

Fenmetozole hydrochloride was administered to children in the age range of 5 to 15 years, having diagnosed MBD. Fenmetozole hydrochloride was employed orally at a daily dosage rate of about 3 mg/kg/day using three divided dosages. (The compound was provided in 25 and 50 mg capsules, and the regimen adjusted to approximate 3 mg/kg daily for each child).

For comparison, methylphenidate (Ritalin®—CIBA) was used at a recommended dosage rate of 0.6 mg/kg/day. EEG's were taken and recorded both pre-drug and post drug so that drug effect could be analyzed against the individual subjects' own pre-drug (untreated) EEG as a baseline. EEG analyses included both resting analyses (discrete wave band analyses, signal ratio, etc.) and evoked potential studies (visual and auditory evoked responses). Additionally, cross-over studies were conducted in which a child was tested on administration of one drug for 4 days, then with the other drug for 4 days (after an intervening "wash out" period of three weeks without any drug, so that fenmetozole hydrochloride and methylphenidate could be compared in the same child. Thirteen subjects were tested. In each case methylphenidate was administered first so that any "carry over" drug effect still present after the "wash out" period would tend to bias the study against fenmetozole hydrochloride. The studies indicated that fenmetozole was at least as effective as methylphenidate in alleviating MBD, as indicated by EEG normalization in both the resting and evoked potential studies. In general, methylphenidate produced more pronounced improvement in resting analysis than in evoked potential, while fenmetozole produced marked improvement in evoked response and less effect on resting analysis. No significant effect on blood pressure was noted. Pulse rates were increased after methylphenidate treatment, but not after fenmetozole.

EXAMPLE 2

To assess drug abuse potential, fenmetozole hydrochloride was tested in comparison to methylphenidate to examine the ability of each compound to maintain a self-injection reponse in monkeys which had been trained to self-inject codeine. Differences in the self-injection reinforcement properties are indicative of a difference in the abuse potential of drugs. Woods and Tessel, Science, 185, 1067–9 (1974) and Tessel and Woods, Psychopharmacologia, 43, 239–244 (1975). Methylphenidate has been reported to maintain self-injection responses. Johansen and Schuster, J. Pharmacol. Exptl. Therap. 193; 676–688 (1975).

Three rhesus monkeys were prepared and trained to self-inject codeine (0.3 mg/kg/injection) in accordance with known procedures. Doses of fenmetozole hydrochloride (0.01 to 0.32 mg/kg/injection) and methylphenidate (0.003 to 0.32 mg/kg/injection) were alternated in each monkey and the responses compared to response produced with codeine and with normal saline. Methylphenidate at 0.003 mg/kg/injection produced response rates similar to those produced by saline (less than 0.05 response per second); 0.01 mg/kg/injection increased self-injection response rates and the maximal self-injection rate (comparable to the codeine rate) was found at 0.03 mg/kg/injection. Larger doses reduced the rate from its maximum of 2.0–2.5 responses/second to about 1.5 responses/second. Fenmetozole hydrochloride had a much lower effect than methylphenidate at all doses. The maximal response to fenmetozole was less than 0.5 response/second at 0.10 mg/kg/injection, and was less than two standard deviation units from the response to normal saline.

These results show that fenmetozole does not produce significant self-injection responses when compared to methylphenidate, indicating the fenmetozole lacks significant abuse potential. In other studies, fenmetozole has not been found to cause hallucinogenic side effects.

While some EEG studies in normal adults have indicated some similarities between fenmetozole and methylphenidate, the comparative effect of the two on MBD in children, and other studies indicate significant differences in the psychopharmacological effects of the two drugs.

What is claimed is:

1. A method for alleviating Minimal Brain Dysfunction in children comprising administering internally to a child suffering from Minimal Brain Dysfunction an amount of an imidazoline compound effective to alleviate said condition, the imidazoline compound being selected from the group consisting of 2-[(3,4-dichlorophenoxy)-methyl]-2-imidazoline and a pharmaceutically-acceptable salt thereof.

2. The method of claim 1 wherein the compound is 2-[3,4-dichlorophenoxy)methyl]-2-imidazoline hydrochloride.

3. The method of claim 2 wherein the compound is administered orally at a daily dosage rate of from about 0.5 to about 10 mg/kg/day.

* * * * *